United States Patent
Han et al.

(10) Patent No.: US 11,767,344 B2
(45) Date of Patent: *Sep. 26, 2023

(54) PHARMACEUTICALLY ACCEPTABLE SALTS OF POLYPEPTIDES AND METHODS OF INHIBITING THE INTERACTION BETWEEN PSD-95 AND N-METHYL-D-ASPARTIC ACID RECEPTOR (NMDAR)

(71) Applicant: BIOCELLS (BEIJING) BIOTECH CO., LTD., Beijing (CN)

(72) Inventors: Huamin Han, Beijing (CN); Yujia Tian, Beijing (CN); Hongjun Jia, Beiing (CN)

(73) Assignee: BIOCELLS (BEIJING) BIOTECH CO., LTD., Beijing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/628,083

(22) PCT Filed: Jul. 5, 2017

(86) PCT No.: PCT/CN2017/091792
§ 371 (c)(1),
(2) Date: Mar. 11, 2020

(87) PCT Pub. No.: WO2019/006690
PCT Pub. Date: Jan. 10, 2019

(65) Prior Publication Data
US 2020/0385425 A1 Dec. 10, 2020

(51) Int. Cl.
*A61K 38/00* (2006.01)
*A61K 38/39* (2006.01)
*C07K 7/00* (2006.01)
*C07K 14/00* (2006.01)
*C07K 4/00* (2006.01)
*C07K 14/475* (2006.01)
*C07K 14/48* (2006.01)
*C07K 7/08* (2006.01)
*A61P 9/10* (2006.01)
*A61K 9/19* (2006.01)
*A61K 47/22* (2006.01)
*A61K 47/26* (2006.01)

(52) U.S. Cl.
CPC ............. *C07K 7/08* (2013.01); *A61K 9/19* (2013.01); *A61K 38/00* (2013.01); *A61K 47/22* (2013.01); *A61K 47/26* (2013.01); *A61P 9/10* (2018.01); *C07K 2319/10* (2013.01)

(58) Field of Classification Search
CPC .... A61K 38/08; A61K 38/1787; A61K 38/00; A61K 38/10; A61K 38/16; A61K 9/19; A61K 47/64; A61K 47/42; A61P 9/10; A61P 25/00; A61P 25/08; A61P 25/22; A61P 25/28; C07K 2319/10; C07K 2319/00; C07K 7/06; C07K 16/1072; C07K 14/00; C07K 2/00; C07K 7/08
See application file for complete search history.

(56) References Cited

U.S. PATENT DOCUMENTS

| | | | | |
|---|---|---|---|---|
| 7,332,571 | B2* | 2/2008 | Miao | A61P 35/00 530/333 |
| 7,385,028 | B2* | 6/2008 | Miao | C07D 317/28 530/333 |
| 8,008,253 | B2* | 8/2011 | Tasker | A61P 25/22 514/8.3 |
| 8,288,345 | B2* | 10/2012 | Belmares | C07K 7/06 514/17.4 |
| 8,536,129 | B2* | 9/2013 | Tasker | A61K 38/07 514/17.5 |
| 8,685,925 | B2* | 4/2014 | Tymianski | A61K 38/07 514/17.7 |
| 8,933,013 | B2* | 1/2015 | Tymianski | A61K 45/06 514/1.1 |
| 9,061,070 | B2* | 6/2015 | Belmares | A61P 43/00 |
| 9,073,990 | B2* | 7/2015 | Paas | A61K 47/65 |
| 9,161,965 | B2* | 10/2015 | Gurd | A61K 45/06 |
| 9,163,227 | B2* | 10/2015 | Annathur | C12N 9/96 |
| 11,229,675 | B2* | 1/2022 | Lu | A61P 9/00 |
| 2005/0019841 | A1 | 1/2005 | Garman et al. | |
| 2005/0059597 | A1 | 3/2005 | Tymianski | |
| 2005/0282743 | A1 | 12/2005 | Lu et al. | |
| 2006/0148711 | A1* | 7/2006 | Lu | C07K 5/1021 530/330 |

(Continued)

FOREIGN PATENT DOCUMENTS

| CN | 101134780 A | 3/2008 |
|---|---|---|
| CN | 101490081 A | 7/2009 |

(Continued)

OTHER PUBLICATIONS

The factsheet of "UniProt: R6TGQ0_9STAP", Nielsen et al., published 2012.*

(Continued)

*Primary Examiner* — Chang-Yu Wang
(74) *Attorney, Agent, or Firm* — KILPATRICK TOWNSEND & STOCKTON LLP

(57) ABSTRACT

There is provided in the present application a pharmaceutically acceptable salt of a polypeptide and a pharmaceutical composition comprising the same, wherein the polypeptide comprises the amino acid sequence YEKLLDTEI (SEQ ID NO:1) or a functional variant thereof.

18 Claims, 4 Drawing Sheets
Specification includes a Sequence Listing.

(56) References Cited

U.S. PATENT DOCUMENTS

| | | | | |
|---|---|---|---|---|
| 2007/0061916 | A1* | 3/2007 | Kovalic | C07K 14/415 800/278 |
| 2008/0153979 | A1* | 6/2008 | Miao | A61K 47/34 525/56 |
| 2008/0177027 | A1* | 7/2008 | Miao | C07D 307/88 530/300 |
| 2008/0274977 | A1* | 11/2008 | Belmares | C07K 14/70571 514/17.7 |
| 2009/0036376 | A1* | 2/2009 | Tasker | A61P 25/22 514/9.7 |
| 2009/0281036 | A1 | 11/2009 | Meyer | |
| 2010/0062985 | A1 | 3/2010 | Belmares et al. | |
| 2010/0160240 | A1* | 6/2010 | Gurd | A61K 45/06 514/1.1 |
| 2011/0039758 | A1* | 2/2011 | Lu | C07K 5/081 514/1.2 |
| 2012/0083449 | A1* | 4/2012 | Tasker | A61K 38/1787 514/17.5 |
| 2012/0208764 | A1* | 8/2012 | Tymianski | A61P 9/10 514/17.7 |
| 2012/0252731 | A1* | 10/2012 | Tymianksi | A61P 29/00 514/15.1 |
| 2013/0121915 | A1* | 5/2013 | Paas | C07K 14/245 424/9.1 |
| 2013/0156704 | A1 | 6/2013 | Tymianski | |
| 2013/0172230 | A1* | 7/2013 | Belmares | A61P 9/00 514/1.2 |
| 2014/0323406 | A1* | 10/2014 | Tymianksi | A61K 38/08 514/15.1 |
| 2015/0105324 | A1 | 4/2015 | Shekhar et al. | |
| 2015/0126460 | A1* | 5/2015 | Tymianski et al. | A61K 47/64 514/21.4 |
| 2017/0121381 | A1* | 5/2017 | Offen | C07K 14/4703 |
| 2019/0134143 | A1 | 5/2019 | Lu et al. | |
| 2020/0385423 | A1 | 12/2020 | Han et al. | |

FOREIGN PATENT DOCUMENTS

| | | |
|---|---|---|
| CN | 103533949 A | 1/2014 |
| CN | 106661126 A | 5/2017 |
| CN | 109718363 B | 12/2019 |
| EP | 2175873 B1 | 11/2015 |
| EP | 2616094 B1 | 11/2017 |
| JP | 2011-520900 A | 7/2011 |
| JP | 2012-530057 A | 11/2012 |
| JP | 2012-530060 A | 11/2012 |
| WO | 2003/014303 A2 | 2/2003 |
| WO | 2009/140416 A2 | 11/2009 |
| WO | 2010/144721 A1 | 12/2010 |
| WO | 2010/144742 A2 | 12/2010 |
| WO | 2012/156308 A1 | 11/2012 |
| WO | 2012/176172 A2 | 12/2012 |
| WO | 2015/181756 A1 | 12/2015 |
| WO | 2017/185249 A1 | 11/2017 |
| WO | 2018/068670 A1 | 4/2018 |

OTHER PUBLICATIONS

The factsheet of "R5L168" from the UniProteKB website published 2012, retrieved on Jan. 2, 2021.*
WO 2017185249—English translated version published 2017.*
Harris et al., J. Cell Sci. 2001; 114:3219-3231.*
Lee et al. Cell Commun. Signaling 2010; 8:8. www.biosignaling.com/content/8/1/8.*
Valgardson et al., Protein Sci. 2019; 28:2127-2143.*
Hillier et al. Science, 1999; 284:812-815.*
Tonikian et al. PLoS Biology, 2008; 6: e239, 2043-2059.*
Gunther et al.EP0955308—English translated version, published Nov. 10, 1999.*
Genbank ID4099612; 1994.
Al-Obeidi, et al; Peptide and Peptidomimetic Libraries; Mol. Biotechnol.; 1998; 9:205-223.
Hruby, et al; Synthesis of oligopeptide and peptidomimetic libraries; Curr. Opin. Chem. Biol.; 1997; 1:114-119.
Ostergaard, et al; Peptomers: a versatile approach for the preparation of diverse combinatorial peptidomimetic bead libraries; 1997; Mo. Divers. 3:17-27.
Ostresh, et al; Generation and Use of Nonsupport-Bound Peptide and Peptidomimetic Combinatorial Libraries; 1996; Methods Enzymol. 267:220-234.
Rankin; Cerebral Vascular Accidents in Patients over the Age of 60: II. Prognosis; 1957; Scott Med. J.; 2:200-15.
Mahoney, et al; Functional Evaluation: the Barthel Index; 1965; Maryland State Medical Journal; 14:56-61.
Lees, et al; NXY-059 for Acute Ischemic Stroke; N. Engl. J. Med.; 2006; 354:588-600.
Aarts, et al.; Treatment of Ischemic Brain Damage by Perturbing NMDA Receptor-PSD-95 Protein Interactions; Science; 298:846-850 (Oct. 2002).
Arundine, et al.; Molecular mechanisms of glutamate-dependent neurodegeneration in ischemia and traumatic brain injury; Cell. Mol. Life Sci.; 61:657-668 (2004).
Fan, et al.; Interaction of Postsynaptic Density Protein-95 with NMDA Receptors Influences Excitotoxicity in the Yeast Artificial Chromosome Mouse Model of Huntington's Disease; J. Neuroscience; 29(35):10928-10938 (Sep. 2009).
Park, et al.; Mice lacking the PSD-95-interacting E3 ligase, Dorfin/Rnf19a, display reduced adult neurogenesis, enhanced long-term potentiation, and impaired contextual fear conditioning; Scientific Reports; 5:16410; doi: 10.1038/srep16410 (Nov. 2015).
Bustos, et al.; Epigenetic editing of the Dlg4/PSD95 gene improves cognition in aged and Alzheimer's disease mice; Brain; 140:3252-3268 (2017).
Yin, et al.; PDZ1 inhibitor peptide protects neurons against ischemia via inhibiting GLUK2-PDS-95-module-mediated Fas signaling pathway; Brain Research; 1637:64-70 (2016).
Bach, et al.; A high-affinity, dimeric inhibitor of PSD-95 bivalently interacts with PDZ1-2 and protects against ischemic brain damage; PNAS; 109(9):3317-3322 (2012).
Bratane, et al.; Neuroprotection by Freezing Ischemic Penumbra Evolution Without Cerebral Blood Flow Augmentation With a Postsynaptic Density-95 Protein Inhibitor; Stroke; 42(11):3265-3270 (2011).
Sun, et al.; Effectiveness of PSD95 Inhibitors in Permanent and Transient Focal Ischemia in the Rat; Stroke 39(9):2544-2553 (2011).
Cook, et al.; Treatment of stroke with a PDS-95 inhibitor in the gyrencephalic primate brain; Nature 483:213-217 (Mar. 2012).
Aarts, et al; Treatment of Ischemic Brain Damage by Perturbing NMDA Receptor-PSD-95 Protein Interactions Science; vol. 298; Oct. 25, 2002; 846-850.
Bell, et al; Calmodulin Kinase IV-dependent CREB activation is required for neuroprotection via NMDA receptor-PSD95 disruption; Jour. of Neurochemistry; 2013; 126, 274-287.
European Patent Office; Supplementary European Search Report of Application No. EP 17916979; dated Feb. 15, 2021.
Korean Intellectual Property Office; Notice of Allowance of Patent for Korean Application No. 10-2020-7003472, dated Apr. 20, 2022; 6 pgs.

* cited by examiner

M · · · 1 · · · · 2 · · · · · 3 · · · · 4

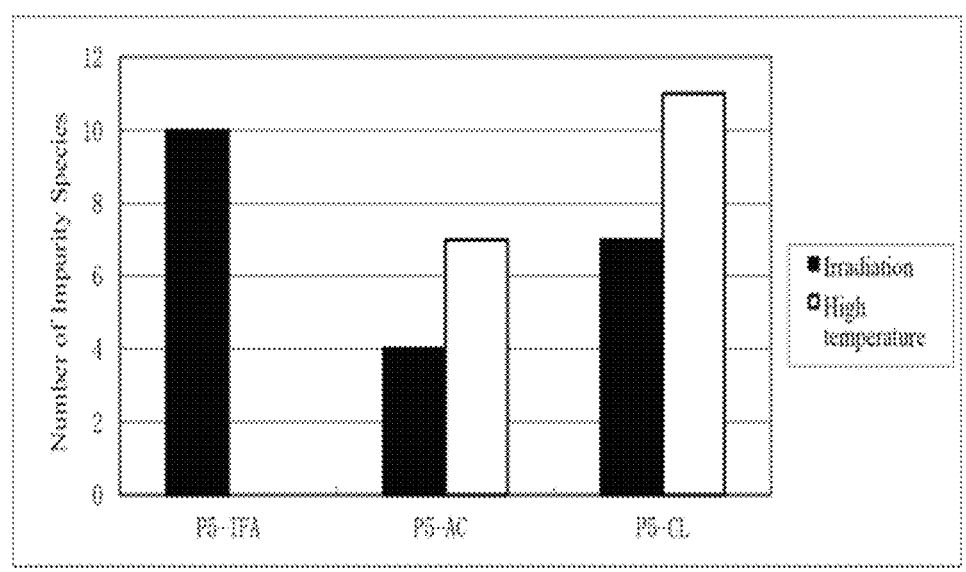
FIGURE 4 –CONT.

SEQUENCE LISTING

```
<160> NUMBER OF SEQ ID NOS: 45

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      P5 active peptide

<400> SEQUENCE: 1

Tyr Glu Lys Leu Leu Asp Thr Glu Ile
1               5

<210> SEQ ID NO 2
<211> LENGTH: 11
<212> TYPE: PRT
<213> ORGANISM: Artificial Sequence
<220> FEATURE:
<223> OTHER INFORMATION: Description of Artificial Sequence: Synthetic
      Tat internalization peptide

<400> SEQUENCE: 2

Tyr Gly Arg Lys Lys Arg Arg Gln Arg Arg Arg
1               5                   10

<210> SEQ ID NO 3
<211> LENGTH: 20
<212> TYPE: PRT
<213> ORGANISM: Artificial Sequence
<220> FEATURE:
<223> OTHER INFORMATION: Description of Artificial Sequence: Synthetic
      P5 chimeric peptide

<400> SEQUENCE: 3

Tyr Gly Arg Lys Lys Arg Arg Gln Arg Arg Arg Tyr Glu Lys Leu Leu
1               5                   10                  15

Asp Thr Glu Ile
            20

<210> SEQ ID NO 4
<211> LENGTH: 20
<212> TYPE: PRT
<213> ORGANISM: Artificial Sequence
<220> FEATURE:
<223> OTHER INFORMATION: Description of Artificial Sequence: Synthetic
      NA-1 peptide

<400> SEQUENCE: 4

Tyr Gly Arg Lys Lys Arg Arg Gln Arg Arg Arg Lys Leu Ser Ser Ile
```

-continued

```
1               5                   10                  15

Glu Ser Asp Val
            20

<210> SEQ ID NO 5
<211> LENGTH: 22
<212> TYPE: PRT
<213> ORGANISM: Artificial Sequence
<220> FEATURE:
<223> OTHER INFORMATION: Description of Artificial Sequence: Synthetic
      YE-NA-1 peptide

<400> SEQUENCE: 5

Tyr Gly Arg Lys Lys Arg Arg Gln Arg Arg Arg Tyr Glu Lys Leu Ser
1               5                   10                  15

Ser Ile Glu Ser Asp Val
            20

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      LDTEI segment of SEQ ID NO: 1

<400> SEQUENCE: 6

Leu Asp Thr Glu Ile
1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      variant of LDTEI segment

<400> SEQUENCE: 7

Leu Asp Thr Glu Leu
1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      variant of LDTEI segment

<400> SEQUENCE: 8

Leu Asp Thr Glu Val
1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      variant of LDTEI segment

<400> SEQUENCE: 9

Leu Asp Thr Asp Ile
1               5
```

```
<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      variant of LDTEI segment

<400> SEQUENCE: 10

Leu Asp Thr Asp Leu
1               5

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      variant of LDTEI segment

<400> SEQUENCE: 11

Leu Asp Thr Asp Val
1               5

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      variant of LDTEI segment

<400> SEQUENCE: 12

Leu Asp Ser Glu Ile
1               5

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
      variant of LDTEI segment

<400> SEQUENCE: 13

Leu Asp Ser Glu Leu
1               5

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
      variant of LDTEI segment

<400> SEQUENCE: 14

Leu Asp Ser Glu Val
1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      variant of LDTEI segment

<400> SEQUENCE: 15
```

Leu Asp Ser Asp Ile
1               5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      variant of LDTEI segment

<400> SEQUENCE: 16

Leu Asp Ser Asp Leu
1               5

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      variant of LDTEI segment

<400> SEQUENCE: 17

Leu Asp Ser Asp Val
1               5

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      variant of LDTEI segment

<400> SEQUENCE: 18

Leu Glu Thr Glu Ile
1               5

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      variant of LDTEI segment

<400> SEQUENCE: 19

Leu Glu Thr Glu Leu
1               5

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      variant of LDTEI segment

<400> SEQUENCE: 20

Leu Glu Thr Glu Val
1               5

<210> SEQ ID NO 21
<211> LENGTH: 5
<212> TYPE: PRT
<213> ORGANISM: Artificial Sequence

```
<220> FEATURE:
<223> OTHER INFORMATION: Description of Artificial Sequence: Synthetic
      variant of LDTEI segment

<400> SEQUENCE: 21

Leu Glu Thr Asp Ile
1               5

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Synthetic
      variant of LDTEI segment

<400> SEQUENCE: 22

Leu Glu Thr Asp Leu
1               5

<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence: Synthetic
      variant of LDTEI segment

<400> SEQUENCE: 23

Leu Glu Thr Asp Val
1               5

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: Synthetic
      variant of LDTEI segment

<400> SEQUENCE: 24

Val Asp Thr Glu Ile
1               5

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      variant of LDTEI segment

<400> SEQUENCE: 25

Val Asp Thr Glu Leu
1               5

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: Synthetic
      variant of LDTEI segment

<400> SEQUENCE: 26

Val Asp Thr Glu Val
1               5
```

```
<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: Synthetic
      variant of LDTEI segment

<400> SEQUENCE: 27

Val Asp Thr Asp Ile
1               5

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: Synthetic
      variant of LDTEI segment

<400> SEQUENCE: 28

Val Asp Thr Asp Leu
1               5

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence: Synthetic
      variant of LDTEI segment

<400> SEQUENCE: 29

Val Asp Thr Asp Val
1               5

<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence: Synthetic
      variant of LDTEI segment

<400> SEQUENCE: 30

Ile Asp Thr Glu Ile
1               5

<210> SEQ ID NO 31
<211> LENGTH: 5
<212> TYPE: PRT
<213> ORGANISM: Artificial Sequence
<220> FEATURE:
<223> OTHER INFORMATION: Description of Artificial Sequence: Synthetic
      variant of LDTEI segment

<400> SEQUENCE: 31

Ile Asp Thr Glu Leu
1               5

<210> SEQ ID NO 32
<211> LENGTH: 5
<212> TYPE: PRT
<213> ORGANISM: Artificial Sequence
<220> FEATURE:
<223> OTHER INFORMATION: Description of Artificial Sequence: Synthetic
      variant of LDTEI segment
```

```
<400> SEQUENCE: 32

Ile Asp Thr Glu Val
1               5

<210> SEQ ID NO 33
<211> LENGTH: 5
<212> TYPE: PRT
<213> ORGANISM: Artificial Sequence
<220> FEATURE:
<223> OTHER INFORMATION: Description of Artificial Sequence: Synthetic
      variant of LDTEI segment

<400> SEQUENCE: 33

Ile Asp Thr Asp Ile
1               5

<210> SEQ ID NO 34
<211> LENGTH: 5
<212> TYPE: PRT
<213> ORGANISM: Artificial Sequence
<220> FEATURE:
<223> OTHER INFORMATION: Description of Artificial Sequence: Synthetic
      variant of LDTEI segment

<400> SEQUENCE: 34

Ile Asp Thr Asp Leu
1               5

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence: Synthetic
      variant of LDTEI segment

<400> SEQUENCE: 35

Ile Asp Thr Asp Val
1               5

<210> SEQ ID NO 36
<211> LENGTH: 5
<212> TYPE: PRT
<213> ORGANISM: Artificial Sequence
<220> FEATURE:
<223> OTHER INFORMATION: Description of Artificial Sequence: Synthetic
      variant of LDTEI segment

<400> SEQUENCE: 36

Ile Glu Thr Glu Ile
1               5

<210> SEQ ID NO 37
<211> LENGTH: 5
<212> TYPE: PRT
<213> ORGANISM: Artificial Sequence
<220> FEATURE:
<223> OTHER INFORMATION: Description of Artificial Sequence: Synthetic
      variant of LDTEI segment

<400> SEQUENCE: 37

Ile Glu Thr Glu Leu
1               5

<210> SEQ ID NO 38
<211> LENGTH: 5
<212> TYPE: PRT
```

```
<213> ORGANISM: Artificial Sequence
<220> FEATURE:
<223> OTHER INFORMATION: Description of Artificial Sequence: Synthetic
      variant of LDTEI segment

<400> SEQUENCE: 38

Ile Glu Thr Glu Val
1               5

<210> SEQ ID NO 39
<211> LENGTH: 5
<212> TYPE: PRT
<213> ORGANISM: Artificial Sequence
<220> FEATURE:
<223> OTHER INFORMATION: Description of Artificial Sequence: Synthetic
      variant of LDTEI segment

<400> SEQUENCE: 39

Ile Glu Thr Asp Ile
1               5

<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence: Synthetic
      variant of LDTEI segment

<400> SEQUENCE: 40

Ile Glu Thr Asp Leu
1               5

<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence: Synthetic
      variant of LDTEI segment

<400> SEQUENCE: 41

Ile Glu Thr Asp Val
1               5

<210> SEQ ID NO 42
<211> LENGTH: 20
<212> TYPE: PRT
<213> ORGANISM: Homo sapiens

<400> SEQUENCE: 42

Phe Asn Gly Ser Ser Asn Gly His Val Tyr Glu Lys Leu Ser Ser Leu
1               5                   10                  15

Glu Ser Asp Val
            20

<210> SEQ ID NO 43
<211> LENGTH: 4
<212> TYPE: PRT
<213> ORGANISM: Homo sapiens

<400> SEQUENCE: 43

Glu Ser Asp Val
1

<210> SEQ ID NO 44
```

```
<211> LENGTH: 5
<212> TYPE: PRT
<213> ORGANISM: Homo sapiens

<400> SEQUENCE: 44

Leu Glu Ser Asp Val
1               5

<210> SEQ ID NO 45
<211> LENGTH: 4
<212> TYPE: PRT
<213> ORGANISM: Homo sapiens

<400> SEQUENCE: 45

Tyr Glu Lys Leu
1
```

PHARMACEUTICALLY ACCEPTABLE SALTS OF POLYPEPTIDES AND METHODS OF INHIBITING THE INTERACTION BETWEEN PSD-95 AND N-METHYL-D-ASPARTIC ACID RECEPTOR (NMDAR)

CROSS-REFERENCE TO RELATED APPLICATIONS

This application is a § 371 National Phase application of PCT/CN2017/091792 filed Jul. 5, 2017, the entire contents of which is incorporated by reference in its entirety for all purposes herein.

SEQUENCE LISTING

The instant application contains a Sequence Listing which has been submitted electronically in ASCII format and is hereby incorporated by reference in its entirety. Said ASCII copy, created on Feb. 28, 2020, is named 093031-1172402-004600US_SL.txt and is 9,980 bytes in size.

TECHNICAL FIELD

The present application generally relates to the biomedical field. In particular, there is provided in the present application pharmaceutically acceptable salts of polypeptides, compositions, and methods for treating, ameliorating, or preventing disorders associated with the nervous system.

BACKGROUND OF THE INVENTION

Nervous system-related diseases manifest in a variety of forms and seriously endanger people's health and quality of life.

Stroke is a common acute cerebrovascular disease in middle-aged and elderly people, and tends to attack the younger. It is one of the top three diseases (cancers, cardiovascular diseases and diabetes) harmful to humans in the world today. It is estimated that nearly three million people die from cerebrovascular diseases every year in China. This number is 4 to 5 times higher than that of the US and European countries, 3.5 times higher than that of Japan, and even higher than that of developing countries such as Thailand and India. The incidence rate increases at a rate of 8.7% per year. The recurrence rate exceeds 30%, and the rate of recurrence within five years reaches 54%. 75% of stroke survivors more or less lose their labor capacity and 40% are severely disabled.

Stroke can be roughly divided into two categories, namely ischemic stroke and hemorrhagic stroke, of which ischemic stroke accounts for 85% of the total number of stroke patients. At present, therapeutic drugs for ischemic stroke mainly includes the following types: vasodilators (such as persantine), drugs that improve microcirculation and expand blood volume (such as low molecular dextran), thrombolytic drugs (such as urokinase), anticoagulant drugs, drugs that prevent platelet aggregation (such as aspirin), Chinese medicine, neuroprotective agents, etc. However, because most of these drugs have issues like significant side effects, potential risks, or insufficient therapeutic efficiency, study on the pathogenesis of stroke and development of drugs directed to the pathogenesis have important social significance for the prevention and treatment of occurrence and development of cerebrovascular diseases.

Stroke is characterized by neuronal cell death in the regions of local ischemia, cerebral hemorrhage, and/or trauma. Neuron death or injuries caused by cerebral ischemia undergo an injury cascade process, i.e., after occurrence of cerebral ischemia, tissue blood perfusion decreases, excitatory neurotransmitters increase which in turn activates NMDA and AMPA receptors, causes ion channel opening and calcium ion influx, and further activates a large number of enzymes to trigger a signal cascade, resulting in nerve cell damage via multiple pathways. Downstream postsynaptic density 95 protein (PSD-95) triggers a series of ischemic injuries through interaction with various proteins, and therefore is a critical factor for injuries caused by cerebral ischemia, and also a potential target for drug therapy. Therefore, development of PSD-95 inhibitors has great medical significance to nervous system injuries caused by various excitatory neurotoxicity, including stroke.

In addition, studies have shown that excitatory neurotransmitter NMDA plays an important role in anxiety, epilepsy, and various neurodegenerative diseases such as Alzheimer's disease, amyotrophic lateral sclerosis (ALS), Parkinson's disease, or Huntington's disease. For example, studies have shown that excessive excitation of the central glutamatergic system can cause anxiety, while the NMDA receptor (NMDAR) is a major element responsible for glutamic acid excitatory neurotoxicity. The onset of epilepsy includes three different but continuous pathophysiological processes, including initiation, maintenance and expansion of seizure discharge, and inhibition of seizure discharge. During this process, excitatory neurotransmitters, such as glutamic acid and aspartic acid, play an important role. In Alzheimer's disease, PSD-95 is involved in the neurotoxic mechanism of the disease through the GluR6-PSD-95-MLK3 pathway. Furthermore, in Huntington's disease, PSD-95 is a mediator of neurotoxicity caused by NMDA receptors and huntingtin mutants. Therefore, development of PSD-95 inhibitors is also important for the treatment, amelioration and prevention of the above diseases.

SUMMARY OF THE INVENTION

In a first aspect, there is provided in the present application a pharmaceutically acceptable salt of a polypeptide, wherein the polypeptide comprises the amino acid sequence YEKLLDTEI (SEQ ID NO:1) or a functional variant thereof.

In some embodiments, the functional variant is a variant generated by one or more conservative substitutions in the LDTEI (SEQ ID NO:6) segment of SEQ ID NO:1.

In some embodiments, the conservative substitution is selected from the group consisting of a substitution between D and E, a substitution among L, V and I, and a substitution between T and S.

In some embodiments, the functional variant is a variant generated by replacing the LDTEI (SEQ ID NO:6) segment of SEQ ID NO:1 with a sequence selected from the group consisting of LDTEL (SEQ ID NO:7), LDTEV (SEQ ID NO:8), LDTDI (SEQ ID NO:9), LDTDL (SEQ ID NO:10), LDTDV (SEQ ID NO:11), LDSEI (SEQ ID NO:12), LDSEL (SEQ ID NO:13), LDSEV (SEQ ID NO:14), LDSDI (SEQ ID NO:15), LDSDL (SEQ ID NO:16), LDSDV (SEQ ID NO:17), LETEI (SEQ ID NO:18), LETEL (SEQ ID NO:19), LETEV (SEQ ID NO:20), LETDI (SEQ ID NO:21), LETDL (SEQ ID NO:22), LETDV (SEQ ID NO:23), VDTEI (SEQ ID NO:24), VDTEL (SEQ ID NO:25), VDTEV (SEQ ID NO:26), VDTDI (SEQ ID NO:27), VDTDL (SEQ ID NO:28), VDTDV (SEQ ID NO:29), IDTEI (SEQ ID NO:30), IDTEL (SEQ ID NO:31), IDTEV (SEQ ID NO:32), IDTDI (SEQ ID NO:33), IDTDL (SEQ ID NO:34), IDTDV (SEQ ID NO:35), IETEI (SEQ ID NO:36), IETEL (SEQ ID NO:37), IETEV (SEQ ID NO:38), IETDI (SEQ ID NO:39), IETDL (SEQ ID NO:40), and IETDV (SEQ ID NO:41).

In some embodiments, the polypeptide is a chimeric peptide comprising an internalization peptide moiety and an active peptide moiety, wherein the active peptide moiety is the amino acid sequence YEKLLDTEI (SEQ ID NO:1) or a functional variant thereof, and the internalization peptide moiety is capable of facilitating uptake of the chimeric peptide by a cell.

In some embodiments, the internalization peptide moiety comprises the amino acid sequence YGRKKRRQRRR (SEQ ID NO:2).

In some embodiments, the chimeric peptide comprises the amino acid sequence YGRKKRRQRRRYEKLLDTEI (SEQ ID NO:3).

In some embodiments, the pharmaceutically acceptable salt is selected from the group consisting of a trifluoroacetate, an acetate, a hydrochloride and a phosphate.

In a second aspect, there is provided in the present application a pharmaceutical composition comprising the pharmaceutically acceptable salt of a polypeptide according to the first aspect, and a pharmaceutically acceptable carrier, excipient, and/or diluent.

In some embodiments, the pharmaceutical composition is a pre-lyophilized formulation, preferably comprising histidine and trehalose.

In some embodiments, the pharmaceutical composition is a lyophilized formulation, preferably prepared by lyophilizing the pre-lyophilized formulation as described above.

In some embodiments, the pharmaceutical composition is a reconstituted formulation, preferably prepared by combining the lyophilized formulation as described above with an aqueous solution.

In some embodiments, the pharmaceutical composition is for use in the treatment, amelioration or prevention of a nervous system injury, a disease or pain associated with a nervous system injury, a neurodegenerative disease, anxiety or epilepsy in a subject.

In some embodiments, the pharmaceutical composition is for use as a neuroprotective agent.

In a third aspect, the present application provides a method for treating, ameliorating or preventing a nervous system injury, a disease or pain associated with a nervous system injury, a neurodegenerative disease, anxiety or epilepsy in a subject, comprising administering to the subject the pharmaceutically acceptable salt of a polypeptide according to the first aspect or the pharmaceutical composition according to the second aspect.

In a fourth aspect, the present application provides use of the pharmaceutically acceptable salt of a polypeptide according to the first aspect or the pharmaceutical composition according to the second aspect in the preparation of a medicament for the treatment, amelioration or prevention of a nervous system injury, a disease or pain associated with a nervous system injury, a neurodegenerative disease, anxiety or epilepsy in a subject, or in the preparation of a neuroprotective agent.

In some embodiments of the second, third or fourth aspect, the nervous system injury is a nervous system injury caused by excitatory neurotoxicity.

In some embodiments, the nervous system injury caused by excitatory neurotoxicity comprises an injury selected from the group consisting of a stroke, a spinal cord injury, an ischemic or traumatic injury to a brain or spinal cord, an injury to a neuron in central nervous system (CNS) including an acute CNS injury, an ischemic stroke or a spinal cord injury, a hypoxia, ischemia, or mechanical injury and an injury caused by a neurodegenerative disease, anxiety, epilepsy or stroke.

In some embodiments of the second, third, and fourth aspects, the neurodegenerative disease is selected from the group consisting of Alzheimer's disease, amyotrophic lateral sclerosis (ALS), Parkinson's disease, and Huntington's disease.

In some embodiments of the second, third or fourth aspect, the nervous system injury or pain is located in the peripheral nervous system or the central nervous system.

In some embodiments of the second, third or fourth aspect, the disease associated with a nervous system injury is a stroke. In some embodiments, the stroke includes an ischemic stroke, a hemorrhagic stroke, and a hemorrhagic stroke converted from an ischemic stroke. In some embodiments, the stroke is an ischemic stroke.

In some embodiments of the second, third or fourth aspect, the subject is a mammal, such as a non-primate or a primate, e.g. human.

DETAILED DESCRIPTION OF THE INVENTION

Figure 1:
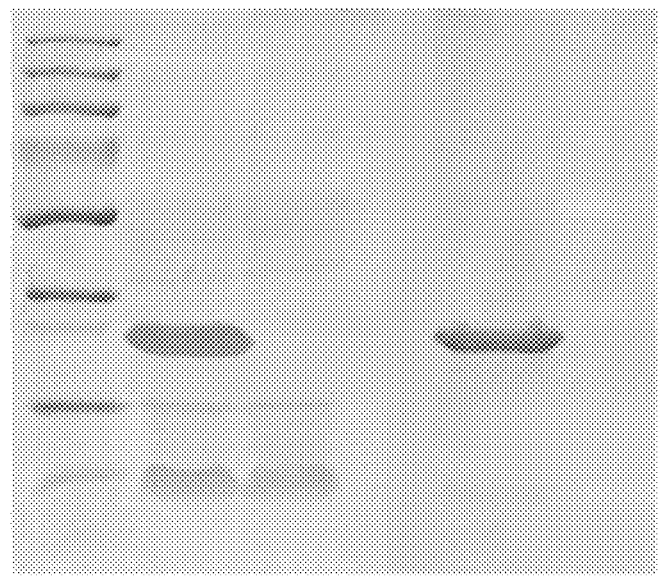
FIG. 1 shows the result of a pull-down assay to detect interaction between P5 and PDZ1/2 domain. M represents a protein molecular weight marker; Lane 1 shows His+PDZ1/2+P5; Lane 2 shows P5 alone; Lane 3 shows His+P5; and Lane 4 shows His+PDZ1/2. The eluted band shown in Lane 1 contains both P5 and PDZ1/2, confirming that P5 is capable of binding to PDZ1/2 domain.

The inventors of the present application have conducted extensive studies on peptides that reduce the injury effects of neurological disorders mediated at least in part by NMDAR excitatory neurotoxicity. Without wishing to be bound by any particular theory, it is believed that such peptides function, at least in part, by inhibiting the interaction between NMDAR and postsynaptic density 95 protein (PSD-95), i.e., as PSD-95 inhibitors. On the basis of the above, the inventors of the present application have intensively considered various targets for the treatment of nervous system diseases, designed and screened polypeptide neuroprotective agents via in vivo and in vitro pharmacological and pharmacodynamics experiments, and further improved the obtained peptides to obtain pharmaceutically acceptable salts of the polypeptides with desirable properties.

Unless otherwise indicated, the terms used in the present application have the meaning as commonly understood by one of ordinary skill in the art.

The one-letter or three-letter abbreviations for amino acids used in the present application are consistent with international conventions.

In the specification and claims, the words "including", "comprising" and "containing" mean "including but not limited to" and are not intended to exclude other parts, additives, components or steps.

In a first aspect, there is provided in the present application a pharmaceutically acceptable salt of a polypeptide, wherein the polypeptide comprises the amino acid sequence YEKLLDTEI (SEQ ID NO:1) or a functional variant thereof.

The term "functional variant" refers to a variant having same or similar biological function and property as its parent. As a non-limiting example, a "functional variant" can be obtained by performing one or more conservative substitutions in the parent. The amino acid sequence YEKLLDTEI (SEQ ID NO:1) or a functional variant thereof is also referred to herein as an "active peptide moiety", which acts as an active moiety in the treatment of a central nervous system injury or in the use as a neuroprotective agent in the present application.

It has been reported in some studies that some active peptides that inhibit the interaction between NMDAR and PSD-95 are based on the structure of NMDAR. For example, NMDAR2B (GenBank ID 4099612) has 20 amino acids FNGSSNGHVYEKLSSLESDV (SEQ ID NO:42) at its C-terminus including the PL motif ESDV (SEQ ID NO:43). Some known active peptides contain a part of the amino acid sequence at the C-terminus of NMDAR2B, thereby competitively inhibiting PSD-95 with NMDAR2B. Studies have suggested that the ESDV (SEQ ID NO: 43) or LESDV (SEQ ID NO:44) segment in the above peptides plays an important role in inhibiting the interaction between NMDAR and PSD-95. The inventors of the present application obtained a peptide sequence YEKLLDTEI (SEQ ID NO:1) via analysis and validation. As compared with the amino acid composition at the C-terminus of the above NMDAR2B, this peptide lacks two residues SS following KL while having the amino acid sequence YEKL (SEQ ID NO:45) extending from the N-terminus of the PL motif. The inventors of the present application proved that this sequence could enhance the interaction of an active peptide with the PDZ1/2 domain. The LDTEI (SEQ ID NO:6) segment at the C-terminus of the peptide relative to the YEKL motif (SEQ ID NO:45) can be modified, and it is expected that such a modification does not affect the activity of the active peptide or may even increase its activity. Accordingly, in some embodiments, the functional variant provided herein is a variant generated by one or more conservative substitutions in the LDTEI (SEQ ID NO:6) segment of SEQ ID NO:1.

In some embodiments, the conservative substitution is selected from the group consisting of a substitution between D and E, a substitution among L, V and I, and a substitution between T and S.

In some more particular embodiments, the functional variant is a variant generated by replacing the LDTEI (SEQ ID NO:6) segment of SEQ ID NO:1 with a sequence selected from the group consisting of LDTEL (SEQ ID NO:7), LDTEV (SEQ ID NO:8), LDTDI (SEQ ID NO:9), LDTDL (SEQ ID NO:10), LDTDV (SEQ ID NO:11), LDSEI (SEQ ID NO:12), LDSEL (SEQ ID NO:13), LDSEV (SEQ ID NO:14), LDSDI (SEQ ID NO:15), LDSDL (SEQ ID NO:16), LDSDV (SEQ ID NO:17), LETEI (SEQ ID NO:18), LETEL (SEQ ID NO:19), LETEV (SEQ ID NO:20), LETDI (SEQ ID NO:21), LETDL (SEQ ID NO:22), LETDV (SEQ ID NO:23), VDTEI (SEQ ID NO:24), VDTEL (SEQ ID NO:25), VDTEV (SEQ ID NO:26), VDTDI (SEQ ID NO:27), VDTDL (SEQ ID NO:28), VDTDV (SEQ ID NO:29), IDTEI (SEQ ID NO:30), IDTEL (SEQ ID NO:31), IDTEV (SEQ ID NO:32), IDTDI (SEQ ID NO:33), IDTDL (SEQ ID NO:34), IDTDV (SEQ ID NO:35), IETEI (SEQ ID NO 36), IETEL (SEQ ID NO:37), IETEV (SEQ ID NO:38), IETDI (SEQ ID NO:39), IETDL (SEQ ID NO:40), and IETDV (SEQ ID NO:41).

In some embodiments, the functional variants disclosed herein also comprise an amino acid sequence having at least 60%, 65%, 70%, 75%, 80%, 85%, 90%, 91%, 92%, 93%, 94%, 95%, 96%, 97%, 98%, 99%, or even higher identity to the peptides as mentioned above. It is known in the art that "identity" between two proteins can be determined by aligning the amino acid sequence of a first protein with the sequence of a second protein which comprises a conservative amino acid substitution relative to the first protein. The degree of identity between two proteins can be determined using computer algorithms and methods well-known to those skilled in the art. The identity between two amino acid sequences is preferably determined by using the BLASTP algorithm.

In some embodiments, the functional variants disclosed herein include those having substitutions, deletions, additions and/or insertions of amino acid residues at 1, 2, 3, 4, 5 or more positions as compared with the peptides as mentioned above, thereby differing from the particular peptides disclosed above.

As described above, a functional variant can differ from a particular peptide disclosed above in one or more substitutions, deletions, additions, and/or insertions. Such variants may be naturally occurring or synthetically produced. For example, one or more of the above-described peptide sequences disclosed herein can be modified and their biological activities can be evaluated following any of a variety of techniques well-known in the art or described herein.

In some embodiments, the polypeptide is a chimeric peptide comprising an internalization peptide moiety and an active peptide moiety, wherein the active peptide moiety is the amino acid sequence YEKLLDTEI (SEQ ID NO:1) or a functional variant thereof, and the internalization peptide moiety is capable of facilitating uptake of the chimeric peptide by a cell.

It should be understood by those skilled in the art that the main purpose of combining an active peptide and an internalization peptide into a chimeric peptide is to better deliver the active peptide to the target of action. Therefore, internalization peptides suitable for the present application are not limited to specific types, as long as the cell-penetrating purpose can be achieved. It should also be understood by those skilled in the art that since the target of action of the active peptide is mainly located inside neuronal cells, it is preferred that the internalization peptide is specifically appropriate to neuronal cells. In some embodiments, the internalization peptide can be a Tat peptide. In some embodiments, the amino acid sequence of a Tat peptide is YGRKKRRQRRR (SEQ ID NO:2). In some embodiments, the chimeric peptide comprises the amino acid sequence YGRKKRRQRRRYEKLLDTEI (SEQ ID NO:3).

It should be appreciated that an internalization peptide may be linked to an active peptide via an amide bond to form a fusion peptide, while they may also be linked via other suitable means, such as chemical bonding. Coupling of two components can be achieved with a coupling agent or a conjugating agent. A great number of such reagents are commercially available and can be found in S. S. Wong, Chemistry of Protein Conjugation and Cross-Linking, CRC Press (1991). Examples of cross-linking reagents include J-succinimide-3-(2-pyridinedithio)propionate (SPOP) or N,N'-(1,3-phenylene)bismaleimide; N,N'-ethylidene-bis-(iodoacetamide) or other such reagents having 6 to 11 carbon methylene bridges (which are relatively specific to thiol groups); and 1,5-difluoro-2,4-dinitrobenzene (which forms an irreversible linkage with an amino group and an tyrosine group). Other cross-linking reagents include P,P'-difluoro-m,m'-dinitrodiphenyl sulfone (which forms an irreversible cross-linkage with an amino group and an phenol group); dimethyl diethylamine hexanoate (which is specific to an amino group); phenol-1,4-disulfonyl chloride (which mainly reacts with an amino group); 1,6-hexamethylene diisocyanate or diisothiocyanate, or phenylazo-p-diisocyanate (which mainly reacts with an amino group; glutaraldehyde (which reacts with several different side chains) and bis-diazotized benzidine (which mainly reacts with tyrosine and histidine).

The active peptide and the fusion peptide with the active peptide fused to an internalization peptide of the present application can be synthesized by solid phase synthesis methods or recombinant methods. Peptidomimetics can be synthesized using a variety of protocols and methods described in scientific literatures and patent literatures, such as Organic Syntheses Collective Volumes, Gilman et al. (ed.) John Wiley & Sons, Inc., NY, al-Obeidi (1998) Mol. Biotechnol. 9:205-223; Hruby (1997) Curr. Opin. Chem. Biol. 1: 114-119; Ostergaard (1997) Mol. Divers. 3: 17-27; Ostresh (1996) Methods Enzymol. 267: 220-234.

Without wishing to be bound by any particular theory, it is expected that a molecule or ion with charge opposite to a drug, when combining with the drug to form a salt, can improve certain undesirable physicochemical or biopharmaceutical properties of the drug, such as changing solubility or dissolution, reducing hygroscopicity, improving stability, or changing melting point for the drug. The final determination of an ideal salt form requires proper balance between physicochemical properties and biopharmaceutical properties. Requirements, e.g. solubility, hygroscopicity, and stability to environmental factors in different states, should be given priority in selecting a pharmaceutically acceptable salt form of a drug. The pharmaceutically acceptable salts of the polypeptides of the present application may be in any suitable pharmaceutically acceptable salt form. In some embodiments, the pharmaceutically acceptable salt of the polypeptide is a trifluoroacetate. In some embodiments, the pharmaceutically acceptable salt of the polypeptide is an acetate. In some embodiments, the pharmaceutically acceptable salt of the polypeptide is a hydrochloride. In some embodiments, the pharmaceutically acceptable salt of the polypeptide is a phosphate. In some particular embodiments, the pharmaceutically acceptable salt of the polypeptide is an acetate or a hydrochloride.

In a second aspect, there is provided in the present application a pharmaceutical composition comprising the pharmaceutically acceptable salt of a polypeptide as described in the first aspect, and a pharmaceutically acceptable carrier, excipient, and/or diluent.

The compounds described herein can be prepared in the form of a lyophilized formulation. In some embodiments, the present application provides a lyophilized formulation. The lyophilized formulation can be prepared from a pre-lyophilized formulation by lyophilization, which contains at least an active ingredient, a buffer, a filler and water, wherein the active ingredient is the compound of the present application or a pharmaceutically acceptable salt thereof. In some embodiments, a preferred buffer is histidine. Other buffers can be selected from succinate, citrate, gluconate, acetate, phosphate, Tris, etc. The filler provides a structure to the lyophilized compound. In some embodiments, the filler is selected from mannitol, trehalose, dextran-40, glycine, lactose, sorbitol, sucrose, and the like, with trehalose being preferred. In some embodiments, the lyophilized formulation of the present application comprises a compound described above, or a pharmaceutically acceptable salt thereof, and histidine and trehalose.

The lyophilized formulation can be reconstituted. That is, the lyophilized formulation is rehydrated with a solution to form a solution of particles that are invisible to naked eyes. In some embodiments, the present application provides a reconstituted formulation prepared by combining a lyophilized formulation with an aqueous solution. In some embodiments, the aqueous solution is water for injection. In some embodiments, the aqueous solution is a physiological saline.

The term "lyophilization" relates to a process in which the raw materials to be dried are first frozen and then sublimed in a vacuum environment to remove ice or frozen solvents.

In some embodiments, a pharmaceutically acceptable salt of a polypeptide disclosed herein can be administered in the form of a pharmaceutical composition. The pharmaceutical composition can be prepared by conventional methods, e.g., mixing, dissolving, granulating, tableting, milling, emulsifying, encapsulating, capturing or lyophilizing.

The pharmaceutical composition can be formulated in a conventional manner using one or more physiologically acceptable carriers, diluents, excipients or ingredients suitable for preparing a pharmaceutically acceptable salt of a polypeptide into a pharmaceutically acceptable formulation. Proper formulation depends on chosen administration routes.

In some embodiments, the administration can be parenteral, intravenous, oral, subcutaneous, intraarterial, intracranial, intrathecal, intraperitoneal, topical, intranasal, or intramuscular administration. Intravenous administration is preferred.

In some embodiments, the pharmaceutical composition for parenteral administration is preferably sterile and substantially isotonic. For injection, a pharmaceutically acceptable salt of a polypeptide can be formulated in an aqueous solution, preferably in a physiologically compatible buffer such as Hank's solution, Ringer's solution, or physiological saline or acetate buffer (to reduce discomfortableness at the injection site). The solution may contain formulating agents such as suspending, stabilizing and/or dispersing agents.

Alternatively, a pharmaceutically acceptable salt of a polypeptide may be in the form of a powder for re-constitution with a suitable vehicle, such as sterile non-pyrogenic water, prior to use.

For transmucosal administration, penetrants appropriate for penetrating the barrier of interest are used in the formulation. This administration route can be used to deliver a compound to the nasal cavity or for sublingual administration.

In some embodiments, for oral administration, a pharmaceutically acceptable salt of a polypeptide can be formulated with a pharmaceutically acceptable carrier into tablets, pills, troches, capsules, liquids, gels, syrups, slurries, suspensions or the like, for oral ingestion by a patient to be treated. For oral solid formulations such as powders, capsules and tablets, suitable excipients include fillers such as sugars such as lactose, sucrose, mannitol and sorbitol; cellulose preparations such as corn starch, wheat starch, rice starch, potato starch, gelatin, tragacanth, methylcellulose, carboxypropylmethylcellulose, sodium carboxymethylcellulose and/or povidone (PVP); granulating agents and binders. If required, a disintegrating agent, such as crosslinked polyvinylpyrrolidone, agar, or alginic acid or a salt thereof (such as sodium alginate), may be added. If required, solid formulations can be coated with sugar or enteric coating using standard techniques. For oral liquid formulations such as suspensions, elixirs and solutions, suitable carriers, excipients or diluents include water, glycerol, oil and alcohol. Furthermore, a flavoring agent, a preservative, a coloring agent, or the like may be added.

In addition to the formulations as described above, a pharmaceutically acceptable salt of a polypeptide can be formulated into a reservoir preparation. Such long-acting formulations can be administered by implantation (for example subcutaneous or intramuscular) or by intramuscular injection. Thus, for example, a compound can be formulated with a suitable polymeric or hydrophobic material (for example, formulated as an emulsion in an acceptable oil) or an ion exchange resin, or formulated as a sparingly soluble derivative, for example, a sparingly soluble salt.

Alternatively, other drug delivery systems can be used. A chimeric peptide can be delivered using liposomes and emulsions. Certain organic solvents, such as dimethyl sulfoxide, can also be used. Additionally, a compound can be delivered using a sustained release system, such as a semipermeable substrate of solid polymers containing a therapeutic agent.

Sustained release capsules may release a chimeric peptide for several weeks or even up to over 100 days depending on their chemical properties. Other strategies for stabilizing a protein can be used depending on the chemical property and biostability of a therapeutic agent.

A pharmaceutically acceptable salt of a polypeptide is used in an amount effective to achieve an intended purpose (e.g., to ameliorate the damaging effect of stroke injuries and related conditions). A therapeutically effective amount means an amount of a pharmaceutically acceptable salt of a polypeptide sufficient to significantly reduce the injuries caused by stroke in patients (or a model animal population) treated with a pharmaceutically acceptable salt of a polypeptide disclosed herein, as compared with the central nervous system injury in a control population of patients (or model animals) not treated with a pharmaceutically acceptable salt of a polypeptide disclosed herein. If a treated patient achieves a better output as compared with a mean output (as determined by infarction volume or disability index) in a comparable patient control population not treated by a method disclosed herein, the amount is also considered to be therapeutically effective. The amount is also considered to be a therapeutically effective amount. If a treated patient shows 2 or fewer disability scores in the Rankin scale and 75 or more scores in the Barthel scale, the amount is also considered to be a therapeutically effective amount. If a treated patient population shows a significantly improved (i.e., less disability) score distribution in the disability scale as compared with comparable untreated populations, the dose is also considered to be therapeutically effective, see Lees et al. N Engl J Med 2006; 354: 588-600. A therapeutically effective regimen represents a combination of a therapeutically effective dose and an administration frequency required to achieve the above intended purpose.

In some embodiments, a preferred dose range of a pharmaceutically acceptable salt of a polypeptide of the present application comprises 0.001 to 20 μmol of the salt per kg patient body weight, optionally 0.03 to 3 μmol of the salt per kg patient body weight, including any value or any range therebetween. In some methods, 0.1-20 μmol of a salt of the present application per kg patient body weight is administered within 6 hours. In some methods, 0.1-10 μmol of a salt of the present application per kg patient body weight is administered within 6 hours, more preferably about 0.3 μmol of a salt of the present application per kg patient body weight is administered within 6 hours. In other instances, the dose range is 0.005 to 0.5 μmol of a salt of the present application per kg patient body weight. The dose per kg body weight can be converted from rats to humans by dividing by 6.2 to compensate for different surface area:mass ratios. In gram, suitable dose of a salt of the present application for human use may include 0.01 to 100 mg/kg patient body weight, or more preferably 0.01 to 30 mg/kg patient body weight or 0.01 to 10 mg/kg, or 0.01 to 1 mg/kg, including any value or any range therebetween.

In some embodiments, the administered amount of a pharmaceutically acceptable salt of a polypeptide depends on the subject being treated, the weight of the subject, the pain severity, the administration mode, and the adjustments by the prescribing physician. Therapy can be repeated when symptoms are detectable or even undetectable. Therapy can be provided alone or in combination with other drugs.

In some embodiments, a therapeutically effective dose of a pharmaceutically acceptable salt of a polypeptide disclosed herein is capable of providing a therapeutic benefit without causing significant toxicity. The toxicity of a chimeric peptide can be determined in cell cultures or experimental animals by standard pharmaceutical procedures, for example by determining $LD_{50}$ (a dose that kills 50% of the population) or $LD_{100}$ (a dose that kills 100% of the population). The dose ratio between toxic effect and therapeutic effect is a therapeutic index. A pharmaceutically acceptable salt of a polypeptide exhibiting a high therapeutic index is preferred (see, for example, Fingl et al, 1975, In: The Pharmacological Basis of Therapeutics, Chapter 1, page 1).

In a second aspect, there is provided in the present application a pharmaceutical composition comprising the pharmaceutically acceptable salt of a polypeptide as described in the first aspect, and a pharmaceutically acceptable carrier, excipient, and/or diluent.

In some embodiments, the pharmaceutical composition is used for treating, ameliorating or preventing a nervous system injury, a disease or pain associated with a nervous system injury, a neurodegenerative disease, anxiety or epilepsy in a subject.

In some embodiments, the pharmaceutical composition is used as a neuroprotective agent.

In some embodiments, the nervous system injury is a nervous system injury caused by excitatory neurotoxicity.

In some embodiments, the nervous system injury caused by excitatory neurotoxicity comprises an injury selected from the group consisting of a stroke, a spinal cord injury, an ischemic or traumatic injury to a brain or spinal cord, an injury to a neuron in central nervous system (CNS) including an acute CNS injury, an ischemic stroke or a spinal cord injury, a hypoxia, ischemia, or mechanical injury and an injury caused by a neurodegenerative disease, anxiety, epilepsy or stroke.

In some embodiments, the pharmaceutical composition is used for treating, ameliorating or preventing an ischemic stroke or a nervous system injury caused by an ischemic stroke. In some embodiments, the pharmaceutical composition is used for treating, ameliorating or preventing a hemorrhagic stroke or a nervous system injury caused by a hemorrhagic stroke. In some embodiments, the pharmaceutical composition is used for treating, ameliorating or preventing a hemorrhagic stroke converted from an ischemic stroke or a nervous system injury caused by a hemorrhagic stroke converted from an ischemic stroke.

Stroke is a condition caused by impaired blood flow in the CNS. Possible causes include embolism, bleeding, and thrombosis. Some neuronal cells die immediately due to impaired blood flow. These cells release their component molecules (including glutamic acid), which in turn activate NMDA receptors, which increase intracellular calcium levels and intracellular enzyme levels, resulting in death of more neuronal cells (excitatory neurotoxicity cascade amplification). The death of CNS tissues is called as infarction. An infarction volume (i.e., the volume of dead neuronal cells in the brain caused by stroke) can be used as an indicator of the extent of pathological injuries caused by stroke. Symptomatic effects depend on both the infarction volume and the location of the infarction in the brain. A disability index can be used as a measure of symptomatic injuries, such as the Rankin Stroke Outcome Scale (Rankin, Scott Med J; 2: 200-15 (1957) and the Barthel Index. The Rankin Scale is based on a direct assessment of a patient's systemic condition as follows.
0: completely no symptom.
1: with symptoms, but no significant disability; able to perform all daily work and activities.
2: minor disability; unable to perform all previous activities, but able to take care of their own affairs without help.
3: moderate disability that requires some help, but able to walk without help.
4: moderate to severe disability, unable to walk without help, and unable to take care of their own body requirements without help.
5: severe disability; bedridden, incontinence, and requiring lasting care and attention.

The Barthel Index is based on a series of questions about the patient's ability to perform 10 basic daily living activities, which are scored between 0 and 100, with lower scores indicating more disability (Mahoney et al., Maryland State Medical Journal) 14:56-61 (1965).

Alternatively, stroke severity/output can be measured using the NIH Stroke Scale, which is available on the World Wide Web at ninds.nih.gov/doctors/NIH_Stroke_Scale-_Booklet.pdf. The Scale is based on a patient's ability to perform 11 sets of functions, including assessment of a patient's consciousness, movement, feeling, and language function levels.

An ischemic stroke more clearly specifies a type of stroke caused by blockage of blood flow to the brain. The potential pathology for such blockages is most commonly associated with the occurrence of fat deposits along the walls of blood vessels. This condition is called as atherosclerosis. These fat deposits can cause two types of obstruction. Cerebral thrombosis refers to a thrombus (blood clot) formed in a blocked part of a blood vessel. "Brain embolism" usually means that various emboli in the blood (such as a wall thrombus in the heart, atherosclerotic plaque, fat, tumor cells, fibrocartilage or air) enter the cerebral artery along with blood flow to block blood vessels. When the collateral circulation is not sufficient for compensation, it causes ischemic necrosis of brain tissue to which the artery supplies blood, and focal neurologic impairment. The second important cause of embolism is irregular heartbeats called arterial fibrillation. This causes a condition that a blood clot can be formed in the heart, and then moves and transfers to the brain. Other potential causes of an ischemic stroke are hemorrhage, thrombosis, arterial or venous severing, cardiac arrest, shock from any causes (including bleeding), and iatrogenic causes, such as direct surgical injuries to cerebral blood vessels or blood vessels going to the brain or cardiac surgery. Ischemic strokes account for approximately 83% of all stroke cases.

Several other neurological disorders can also cause neuron death through NDMAR-mediated excitatory neurotoxicity. These disorders include neurodegenerative diseases, anxiety, epilepsy, hypoxia, damage to the CNS irrelevant to a stroke, such as traumatic brain injury and spinal cord injury. Accordingly, in some embodiments, the pharmaceutical composition is used for treating, ameliorating or preventing neurodegenerative diseases, anxiety or epilepsy, wherein the neurodegenerative diseases may comprise Alzheimer's disease, amyotrophic lateral sclerosis (ALS), Parkinson's disease or Huntington's disease.

In some embodiments, the pharmaceutical composition is used as a neuroprotective agent.

In a third aspect, there is provided in the present application a method for treating, ameliorating or preventing a nervous system injury, a disease or pain associated with a nervous system injury, a neurodegenerative disease, anxiety or epilepsy in a subject, comprising administering to the subject the pharmaceutically acceptable salt of a polypeptide as described in the first aspect or a pharmaceutical composition as described in the second aspect.

In some embodiments, the nervous system injury is a nervous system injury caused by excitatory neurotoxicity, wherein the injury or pain may be located in the peripheral nervous system or the central nervous system. In some embodiments, the nervous system injury caused by excitatory neurotoxicity comprises an injury selected from the group consisting of a stroke, a spinal cord injury, an ischemic or traumatic injury to a brain or spinal cord, an injury to a neuron in central nervous system (CNS) including an acute CNS injury, an ischemic stroke or a spinal cord injury, a hypoxia, ischemia, or mechanical injury and an injury caused by a neurodegenerative disease, anxiety, epilepsy or stroke.

In some embodiments, the neurodegenerative disease includes Alzheimer's disease, amyotrophic lateral sclerosis (ALS), Parkinson's disease, or Huntington's disease.

In some embodiments, the disease is an ischemic stroke or a nervous system injury caused by an ischemic stroke. In some embodiments, the disease is a hemorrhagic stroke or a nervous system injury caused by a hemorrhagic stroke. In some embodiments, the disease is a hemorrhagic stroke converted from an ischemic stroke or a nervous system injury caused by a hemorrhagic stroke converted from an ischemic stroke.

In a fourth aspect, there is provided in the present application use of the pharmaceutically acceptable salt of a polypeptide as described in the first aspect, or a pharmaceutical composition as described in the second aspect, in the preparation of a medicament for treating, ameliorating or preventing a nervous system injury, a disease or pain associated with a nervous system injury, a neurodegenerative disease, anxiety or epilepsy in an subject, or in the preparation of a neuroprotective agent.

In some embodiments, the nervous system injury is a nervous system injury caused by excitatory neurotoxicity, wherein the injury or pain may be located in the peripheral nervous system or the central nervous system. In some embodiments, the nervous system injury caused by excitatory neurotoxicity comprises an injury selected from the group consisting of a stroke, a spinal cord injury, an ischemic or traumatic injury to a brain or spinal cord, an injury to a neuron in central nervous system (CNS) including an acute CNS injury, an ischemic stroke or a spinal cord injury, a hypoxia, ischemia, or mechanical injury and an injury caused by a neurodegenerative disease, anxiety, epilepsy or stroke.

In some embodiments, the neurodegenerative disease includes Alzheimer's disease, amyotrophic lateral sclerosis (ALS), Parkinson's disease, or Huntington's disease.

In some embodiments, the disease is an ischemic stroke or a nervous system injury caused by an ischemic stroke. In some embodiments, the disease is a hemorrhagic stroke or a nervous system injury caused by a hemorrhagic stroke. In some embodiments, the disease is a hemorrhagic stroke converted from an ischemic stroke or a nervous system injury caused by a hemorrhagic stroke converted from an ischemic stroke.

The term "subject", as used herein, refers to animals including birds, reptiles, and mammals. In some embodiments, the subject is a mammal, including primates and non-primates, such as human, chimpanzees, bovines, equines, pigs, sheep, goats, dogs, cats, and rodent animals such as rats and mice.

It should be understood that the foregoing detailed description only aims to help those skilled in the art to more clearly understand the present application, but not intended to limit the present application in any way. Those skilled in the art can make various modifications and changes to the described embodiments.

EXAMPLES

The following examples are provided only to illustrate some embodiments of the present application without any purpose or nature of limitation.

Example 1: Screening of Active Peptide Molecules

The Tat transmembrane peptide YGRKKRRQRRR (SEQ ID NO:2) was selected based on reported study results, and ligated to various numbers of amino acids to form a peptide library. The chimeric peptide molecules in the peptide library were tested for interaction with the PDZ1/2 domain expressed and purified in vitro, and the polypeptides were preliminarily screened for the strength of interaction force.

The immobile phase molecule (ligand) was PDZ1/2 protein with a molecular weight of approximately 20 kD at a concentration of 2 mg/ml. The mobile phase molecule (analyte) was a polypeptide to be screened with a molecular weight of approximately 2 kD at a concentration of 10 mg/ml. The CM5 chip was used for fixation using a Biacore 3000 instrument. The electrophoresis buffer was PBS plus 0.005% Tween 20. Fixation was carried out using an amino coupling method. The concentration of the ligand was 10 μg/ml. The fixation buffer was 10 mM sodium acetate, pH 4.0. The fixed amount was 1400 RU, which was fixed to flow cell 2. The used flow rate was 10 μl/ml and the ligand was loaded for 1 minute. 10 mM Gly at pH 2.0+2.5 was used as a regenerant. Regeneration was carried out at a flow rate of 30 μl/min. The loading time was 30 s.

Kinetic analysis was performed using the following conditions.
Control Channel: flow cell 1
Electrophoresis Buffer: PBS
Mode: Kinetic Analysis Wizard
Concentration Gradients: 6.25 nM, 12.5 nM, 25 nM, 50 nM, 100 nM, 200 nM, 400 nM
Loading Time: 1 minute
Dissociation Time: 2 min
Flow Rate: 30 μl/min The data was fitted using the fitting software Biaevaluation 4.1. The fitting model was a 1:1 binding model. The dissociation constant KD value was inversely proportional to the interaction force.

By screening, a chimeric peptide having strong capability of interacting with the PDZ1/2 domain was obtained, and named as P5. The sequence of the chimeric peptide was shown below.

P5:
(SEQ ID NO: 3)
YGRKKRRQRRRYEKLLDTEI

In order to directly compare with a similar chimeric peptide in the reported studies, a control chimeric peptide NA-1 was introduced with the following sequence.

NA-1:
(SEQ ID NO: 4)
YGRKKRRQRRRKLSSIESDV

Furthermore, in view of the structural difference between P5 and NA-1, a chimeric peptide YE-NA-1 having two residues of YE added to the N-terminus of the active peptide of the chimeric peptide NA-1 was additionally introduced, and its sequence is shown below.

YE-NA-1:
(SEQ ID NO: 5)
YGRKKRRQRRRYEKLSSIESDV

The chimeric peptides NA-1, YE-NA-1 and P5 were simultaneously subjected to tests for interaction with the PDZ1/2 domain as mentioned above, and the results were shown in Table 1 below.

TABLE 1

Determination of interaction force between three chimeric peptides and PDZ1/2 domain

| chimeric peptides | NA-1 | YE-NA-1 | P5 |
|---|---|---|---|
| KD (M) | 7.53E−08 | 5.44E−08 | 2.99E−08 |

As shown in Table 1, the chimeric peptides YE-NA-1 and P5 interacted more strongly with the PDZ1/2 domain as compared with the control chimeric peptide NA-1, and the performance of P5 was even better. Therefore, based on the inventors' speculation, the additional two amino acid residues YE at the N-terminus of the active peptide caused certain improved effect on the interaction of the polypeptide with the PDZ1/2 domain. Furthermore, P5 lacked two weakly hydrophobic serines (SS) relative to the carboxy terminus of YE-NA-1. Based on the inventors' speculation, this may further increase the interaction of the polypeptide with the PDZ1/2 domain.

Example 2: Pull-Down Assay to Verify the Interaction of P5 with PDZ1/2 Domain

To confirm that P5 can interact with the PDZ1/2 domain, a pull-down assay was performed.

The column was equilibrated with 100 μl of His beads and 1 ml of MCAC-0 buffer for 5 min and then shaked at 4° C. The mixture was centrifuged at 5,000 g for 1 minute at 4° C., and the supernatant was discarded. 1 mg of PDZ1/2 protein was added to the mixture, and a buffer was added to reach the volume of 1 ml. The mixture was spun for binding for 1 hour at 4° C. The mixture was centrifuged at 5000 g for 1 minute at 4° C., and the supernatant was discarded. The mixture was washed three times with 1 ml of MCAC-0 buffer with each time for 5 minutes (at 4° C., washing with shaking). 1 mg of P5 protein was added to the mixture, and a buffer was added to reach the volume of 1 ml. The mixture was spun for binding for 2 hours at 4° C. The mixture was centrifuged at 5000 g for 1 minute at 4° C., and the supernatant was discarded. The mixture was washed three times with 1 ml of lysis buffer with each time for 5 minutes (at 4° C., washing with shaking). 20 μl of MCAC-300 was added after washing. After centrifugation, the eluate was taken for an SDS-PAGE assay. The experimental results were shown in FIG. 1.

As shown in FIG. 1, both P5 and the PDZ1/2 domain were contained in the eluted band of the chimeric peptide P5, thereby confirming that the chimeric peptide P5 can bind to the PDZ1/2 domain.

Example 3: Therapeutic Effects of P5 Salts on a Rat MCAO Model

Based on the chimeric peptide P5 obtained in Examples 1 and 2, the inventors of the present application designed P5-trifluoroacetate (P5-TFA), P5-acetate (P5-Ac), and P5-hydrochloride (P5-Cl), and commissioned Hangzhou Chinese Peptide Co., Ltd. for synthesis. The three prepared P5 salts were tested on a rat MCAO model for their therapeutic effects.

Experimental Animals and Materials

The animals were male adult SD rats (Vittalia) of SPF grade with body weight of 220-250 g.

The instruments included one line scissor, two eye surgery scissors, four curved forceps, 4 #, 5 #surgical sutures, 6×17 triangular needles, a occlusion line (0.26 mm of diameter), and one needle holders. The agents included Enbipu sodium chloride injection solution (Shijiazhuang Group NBP Pharmaceutical Co., Ltd.), chloral hydrate, furosemide (20 mg/vial), gentamicin sulfate (80 mg/vial), cotton swabs, and medical trays.

MCAO Modeling

The focal cerebral ischemia-reperfusion model was prepared according to the reversible middle cerebral artery occlusion (MCAO) suture method proposed by Longa with modifications in view of the anatomical structure of the rat brain. The rats were anesthetized by intraperitoneal administration of 10% chloral hydrate at a dose of 0.3 ml/kg. After anesthetization, a cut was created at the cervical midline, and the common carotid artery (CCA), external carotid artery (ECA) and pterygopalatine artery were exposed. The head portion (0.5 cm) of a monofilament nylon fishing line (0.26 mm) was coated with paraffin and a mark was made at 20 mm. All rats were inserted through the right CCA incision, and the pterygopalatine artery was temporarily clamped to prevent mis-insertion. The length of the occlusion line was about 18-20 mm from the bifurcation of CCA depending on the animal's weight, thereby occluding middle cerebral artery on the right side. The skin was then sewed, and the tail end of the occlusion line was partially fixed to the skin. After a period of ischemia for 2 hours, the occlusion line was carefully pulled out to form a reperfusion. The body temperature was maintained at 37±0.5° C. during the ischemia period and 2 h after reperfusion. The success marker for the model is that the rats, after they awoke from anesthesia, showed paralyzed left limb, unstable standing and turning to one side when their tails were lift up.

Experimental Grouping

The experimental animals were divided into the control group (normal group), model group (normal saline group), positive control drug Enbipu group (NBP), and P5 salt groups. A saline solution, positive control drug Enbipu (2.5 mg/kg), and each P5 salt (10 mg/kg) were respectively administered to respective groups of rats via tail vein injection at 1 hour after ischemia.

Calculation of Infarction Volume

The rats were sacrificed by decapitation at 24 h after administration. The brain tissues were quickly removed and placed in a refrigerator at −20° C. After 10 minutes, the tissues were placed in a room temperature environment. The brains were placed in a rat brain section mold. After the olfactory bulb, cerebellum and low brain stem were removed, the brains were coronally cut five times at 2 mm thickness as shown in the profile to obtain six continuous raw coronal slices. Then, the brain sections were quickly placed in a 5 ml solution containing 2% TTC, and incubated at 37° C. for 30 minutes in the dark, during which the brain sections were flipped once every 5 minutes. With the TTC staining, the normal tissue would be rose red, and the infarcted tissue would be unstained and retained white. Each group of brain sections was arranged neatly, and photographed. The photos were processed by an image analysis system software and statistically analyzed. The infarction area of each brain section was calculated, and multiplied by the thickness of each brain section (2 mm). The products of the infarction area of subject brain section multiplied by the thickness were summed to obtain the cerebral infarction volume for each animal. The volumes were expressed as percentages accounting for the cerebral hemisphere to eliminate the effects of cerebral edema.

Figure 2:
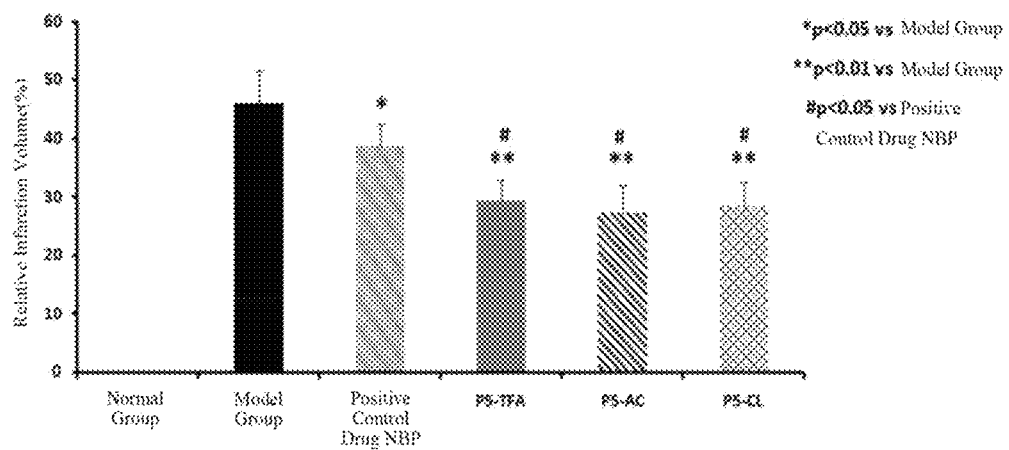
FIG. 2 shows a comparison of experimental data of pharmacodynamics of different salts of the polypeptide in rats.

The experimental results were shown in FIG. 2. The results showed that the administration of P5-TFA, P5-Ac and P5-Cl significantly reduced the cerebral infarction volume in the rats as compared with the model group ($p<0.01$); while as compared with the positive control drug NBP, the effects of administration of P5-TFA, P5-Ac and P5-Cl in reducing the cerebral infarction volume in the rats were significantly superior to that of the positive control drug NBP ($p<0.05$).

Example 4: Determination of Cytotoxicity of P5 Salts

This example tested the cytotoxicity of two polypeptide salts, P5-Ac and P5-Cl in Example 3.

Experimental Materials

Cell line PC12 cells were used. Other experimental materials included a clean bench with vertical laminar flow, a steam sterilizer, a centrifuge, a microscope, a microplate reader, cover slips, blood cell counting plates, a manual counter, an alcohol lamp, pipettors, pipettes, pipette tips, centrifuge tubes, 96-well plates, PBS/saline, high glucose DMEM medium (containing 10% FBS and 1% dual-antibiotics). CCK8 was purchased from Solvay.

Experimental Protocols

Cells at logarithmic phase were digested and seeded into a 96-well plate at a density of $4\times10^4$ cells/well in triplicates, and cultured overnight. The P5 salt (e.g., 5 μM) was formulated in the culture medium. The supernatant in the 96-well plate was discarded, the plate was washed 2-3 times with PBS/physiological saline, and then 100 µl of P5 salt preparation was added to each well. Same P5 salt preparation was also added to the blank control wells (no cell). The cells were cultured for 24 hours. 10 µl of CCK8 was added to each well of the 96-well plate and the plate was incubated for 1 h. The absorbance of each well of the 96-well plate was measured at 450 nm using a microplate reader. Cell viability was calculated from the reads based on the following equation.

Cell viability (%)=(experimental group−corresponding blank control group)/(0 µM experimental group−0 µM blank control group)×100%

Figure 3:
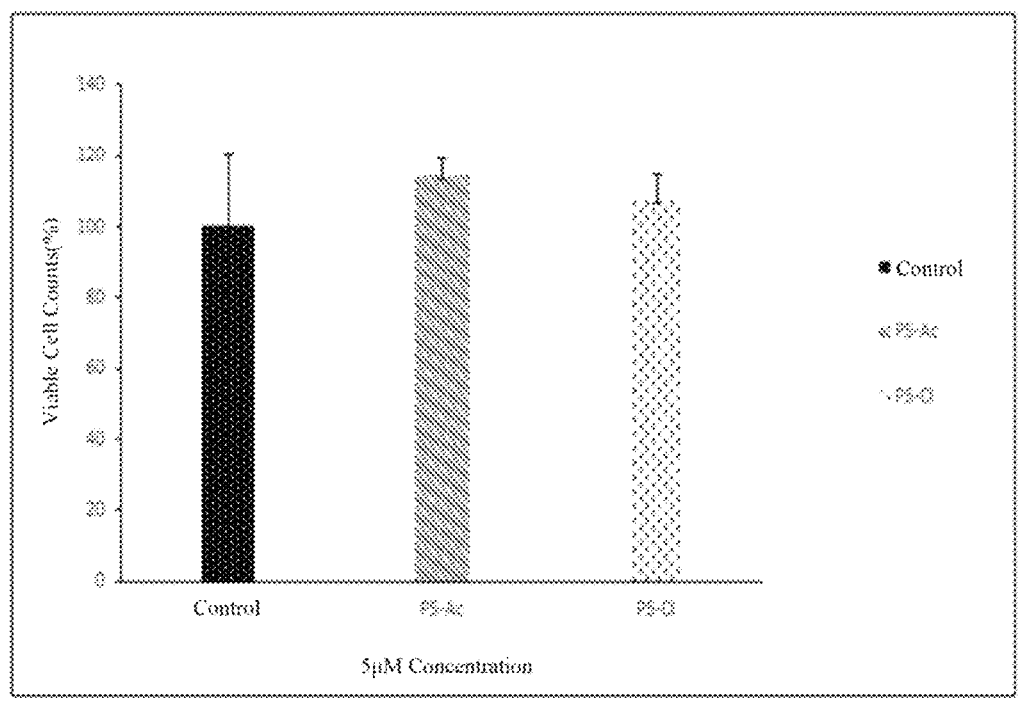
FIG. 3 shows the results of cytotoxicity assays for different salts of the polypeptide.

The experimental results were shown in FIG. 3. The results showed that the two pharmaceutically acceptable salts of the P5 polypeptide, i.e. P5-Ac and P5-Cl, had no significant cytotoxicity at a concentration of 5 µM.

Example 5: Stability of P5 Salts

In this example, the stability of the three P5 salts in Example 3 was tested under various conditions including irradiation, high temperature, and high humidity.

Stability Analysis of P5 Salt Powders

The three P5 salts in Example 3 in their powder form were subjected to treatments with irradiation (3000 Lx)+ultraviolet (UV), high temperature (60° C.), and high humidity (75% RH) for 10 days. After the treatments, the powders were dissolved in water to prepare a solution at a concentration of 2 mg/ml. 10 µl of each solution was accurately measured and injected into a liquid chromatograph, and the chromatograms were recorded. Relevant substances were calculated according to the area normalization method to analyze the content and the number of impurity species.

Instruments and Reagents high performance liquid chromatograph (Agilent, 1260 EZChrom); chromatographic column (Agilent, ZORBAX 300SB-C18 (4.6*250 mm, 5 µm) SN: USHH008416); analytical balance (Sartoris, BT25S); filter membrane (Millipore, 0.45 µm PTFE); acetonitrile (MREDA); water (Aqua); TFA (MREDA); and comprehensive drug stability test box (three-box type) (Shanghai Zuocheng Experimental Instrument Co. Ltd, item no. SHH-3SDT).

Chromatographic Parameters

Mobile phase: A 0.065% TFA-water; B 0.05% TFA-ACN
Detection wavelength $\lambda$=220 nm; flow rate V=1.0 ml/min; temperature T=36° C.
Injection volume Inj=10 ul
Gradient conditions: 0-30 min, B %=5-65%

Result Analysis

The results of the stability analysis of the three P5 salt powders were shown in Table 2 below and panels A and B in FIG. 4.

TABLE 2

|  |  | Hydrochloride | Acetate | Trifluoroacetate |
| --- | --- | --- | --- | --- |
| Irradiation + ultraviolet | Percentage of main peak area | 90.59% | 96.47% | 98.34% |
|  | Number of impurity species | 18 | 14 | 6 |
| High temperature | Percentage of main peak area | 99.50% | 99.79% | 99.56% |
|  | Number of impurity species | 3 | 1 | 3 |
| High humidity | Percentage of main peak area | 99.44% | 95.75% | 99.73% |
|  | Number of impurity species | 3 | 2 | 1 |

Results

After the treatment with irradiation+ultraviolet, the percentages of main peak area and the numbers of impurity species of the three salts were significantly different. The relative stability order was: trifluoroacetate>acetate>hydrochloride.

After the treatment with high temperature, the percentages of the main peak area of the three salts were all above 99.5% without significant difference. Acetate was the most stable in the comparison of the number of impurity species.

After the treatment with high humidity, the percentage of the main peak area of the acetate was significantly reduced. The relative stability order was: trifluoroacetate>hydrochloride>acetate.

In general, the three salts showed good stability under different conditions.

Stability Analysis of P5 Salt Solutions

The three P5 salts in Example 3 were dissolved in water to prepare solutions at a concentration of 2 mg/ml. The solutions were subjected to treatments with irradiation (3000 Lx) and high temperature (60° C.) for 10 days. After the treatments, 10 µl of each solution was accurately measured and injected into a liquid chromatograph, and the chromatograms were recorded. The relevant substances were calculated according to the area normalization method to analyze the content and the number of impurity species.

Instruments and Reagents high performance liquid chromatograph (Agilent, 1260 EZChrom); chromatographic column (Agilent, ZORBAX 300SB-C18 (4.6*250 mm, 5 µm) SN: USHH008416); analytical balance (Sartoris, BT25S); filter membrane (Millipore, 0.45 µm PTFE); acetonitrile (MREDA); water (Aqua); TFA (MREDA); and comprehensive drug stability test box (three-box type) (Shanghai Zuocheng Experimental Instrument Co. Ltd, item no. SHH-3SDT).

Chromatographic Conditions

Mobile phase: A 0.065% TFA-water; B 0.05% TFA-ACN
Detection wavelength $\lambda$=220 nm; flow rate V=1.0 ml/min; temperature T=36° C.
Injection volume Inj=10 µl
Gradient conditions: 0-30 min, B %=5-65%

Result Analysis

Figure 4:
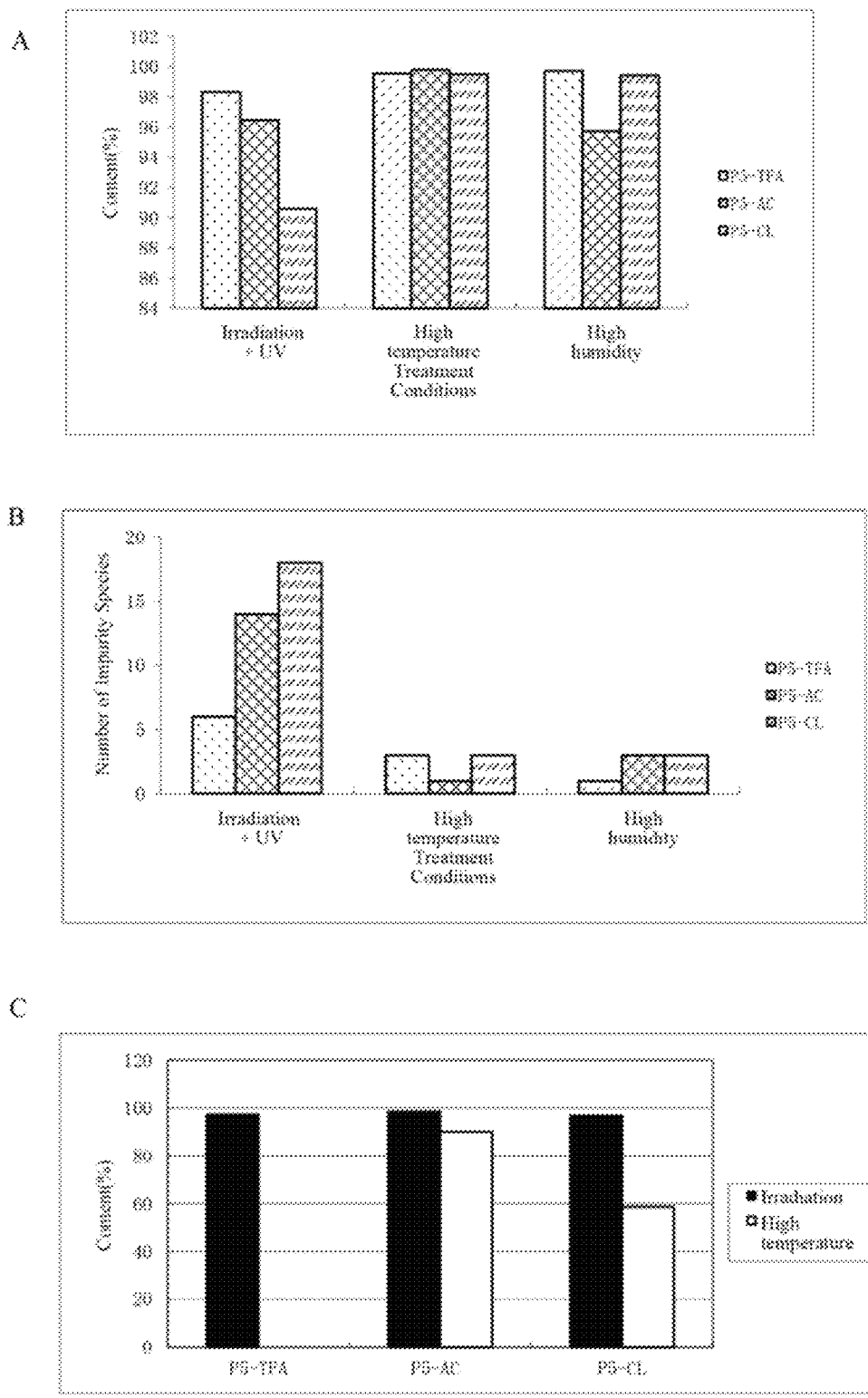
FIG. 4 shows the stability of different salts of the polypeptide, in which panels A and B respectively show the content and number of impurity species of different salts of the polypeptide in solid form after exposure to treatments in including irradiation+UV, high temperature and high humidity; and panels C and D respectively show the content and the number of impurity species of different salts of polypeptide in the form of aqueous solution after being subjected to irradiation and high temperature treatments.

The results of the stability analysis of the aqueous solutions of the three P5 salts were shown in Table 3 and panels C and D in FIG. 4.

TABLE 3

|  |  | Hydrochloride | Acetate | Trifluoroacetate |
| --- | --- | --- | --- | --- |
| Irradiation | Percentage of main peak area | 96.73% | 98.51% | 97.28% |
|  | Number of impurity species | 7 | 4 | 10 |

TABLE 3-continued

|  |  | Hydrochloride | Acetate | Trifluoroacetate |
|---|---|---|---|---|
| High temperature | Percentage of main peak area | 58.63% | 90.07% |  |
|  | Number of impurity species | 11 | 7 |  |

Results

After the treatment with irradiation, the percentages of main peak area and the numbers of impurity species of the three salt solutions were different. The relative stability order was: acetate>trifluoroacetate>hydrochloride.

After the treatment with high temperature, the percentages of main peak area and the numbers of impurity species of the hydrochloride and acetate were different. The relative stability order was: acetate>hydrochloride.

In general, the three salt solutions also showed good stability under different conditions.

All publications and patent documents cited in the Specification are herein incorporated by reference as if each publication or patent were specifically and individually indicated to be incorporated by reference. Various changes and equivalent substitutions can be made to the various embodiments disclosed herein without departing from the true spirit and scope of the disclosure. Any feature, step or embodiment of an embodiment of the present disclosure can be used in combination with any other feature, step or embodiment, unless otherwise stated in the context.

What is claimed is:

1. A pharmaceutically acceptable salt of a peptide, wherein the peptide comprises the amino acid sequence YEKLLDTEI (SEQ ID NO:1) or a functional variant thereof, wherein the functional variant is a variant only having one or more conservative substitutions in YEKLLDTEI (SEQ ID NO:1), wherein the conservative substitution is selected from the group consisting of a substitution between D and E, a substitution among L, V and I, and a substitution between T and S, wherein the peptide or the functional variant thereof is capable of binding to the PSD-95/Discs-large/ZO-1 1/2 domain (PDZ1/2) domain of postsynaptic density 95 protein (PSD-95) and inhibiting the interaction between PSD-95 and N-methyl-D-aspartic acid receptor (NMDAR), and wherein the salt is an acetate.

2. The pharmaceutically acceptable salt of a peptide according to claim 1, wherein the functional variant is a variant generated by one or more conservative substitutions in the LDTEI (SEQ ID NO:6) segment of SEQ ID NO:1, and wherein the conservative substitution is selected from the group consisting of a substitution between D and E, a substitution among L, V and I, and a substitution between T and S.

3. The pharmaceutically acceptable salt of a peptide according to claim 2, wherein the functional variant is a variant generated by replacing the LDTEI (SEQ ID NO:6) segment of SEQ ID NO: 1 with a sequence selected from the group consisting of LDTEL (SEQ ID NO:7), LDTEV (SEQ ID NO:8), LDTDI (SEQ ID NO:9), LDTDL (SEQ ID NO:10), LDTDV (SEQ ID NO:11), LDSEI (SEQ ID NO:12), LDSEL (SEQ ID NO:13), LDSEV (SEQ ID NO:14), LDSDI (SEQ ID NO:15), LDSDL (SEQ ID NO:16), LDSDV (SEQ ID NO:17), LETEI (SEQ ID NO:18), LETEL (SEQ ID NO:19), LETEV (SEQ ID NO:20), LETDI (SEQ ID NO:21), LETDL (SEQ ID NO:22), LETDV (SEQ ID NO:23), VDTEI (SEQ ID NO:24), VDTEL (SEQ ID NO:25), VDTEV (SEQ ID NO:26), VDTDI (SEQ ID NO:27), VDTDL (SEQ ID NO:28), VDTDV (SEQ ID NO:29), IDTEI (SEQ ID NO:30), IDTEL (SEQ ID NO:31), IDTEV (SEQ ID NO:32), IDTDI (SEQ ID NO:33), IDTDL (SEQ ID NO:34), IDTDV (SEQ ID NO:35), IETEI (SEQ ID NO:36), IETEL (SEQ ID NO:37), IETEV (SEQ ID NO:38), IETDI (SEQ ID NO:39), IETDL (SEQ ID NO:40), and IETDV (SEQ ID NO:41).

4. The pharmaceutically acceptable salt of a peptide according to claim 1, wherein the peptide is a chimeric peptide comprising an active peptide moiety and an internalization peptide moiety, and wherein the active peptide moiety is the amino acid sequence YEKLLDTEI (SEQ ID NO:1) or the functional variant thereof, and the internalization peptide moiety is capable of facilitating uptake of the chimeric peptide by a cell.

5. The pharmaceutically acceptable salt of a peptide according to claim 4, wherein the internalization peptide moiety comprises the amino acid sequence YGRKKRRQRRR (SEQ ID NO:2).

6. The pharmaceutically acceptable salt of a peptide according to claim 5, wherein the chimeric peptide comprises the amino acid sequence YGRKKRRQRRRYEKLLDTEI (SEQ ID NO:3).

7. A pharmaceutical composition comprising the pharmaceutically acceptable salt of a peptide according to claim 1, and a pharmaceutically acceptable carrier, excipient and/or diluent.

8. The pharmaceutical composition according to claim 7, wherein the pharmaceutical composition is a pre-lyophilized formulation.

9. The pharmaceutical composition according to claim 8, wherein the pre-lyophilized formulation comprises histidine and trehalose.

10. The pharmaceutical composition according to claim 7, wherein the pharmaceutical composition is a lyophilized formulation.

11. The pharmaceutical composition according to claim 7, wherein the pharmaceutical composition is a reconstituted formulation.

12. A method for inhibiting the interaction between PSD-95 and N-methyl-D-aspartic acid receptor (NMDAR) in a subject in need thereof, wherein the subject suffers from a nervous system injury or pain associated with the nervous system injury; and wherein the nervous system injury is caused by excitatory neurotoxicity mediated by interaction between PSD-95 and NMDAR, comprising administering to the subject the pharmaceutical composition according to claim 7.

13. The method according to claim 12, wherein the nervous system injury caused by excitatory neurotoxicity mediated by interaction between PSD-95 and NMDAR is selected from the group consisting of a stroke, a spinal cord injury, an ischemic or traumatic injury to a brain or spinal cord, an injury to a neuron in central nervous system (CNS) including an acute CNS injury, an ischemic stroke or a spinal cord injury, a hypoxia, ischemia, or mechanical injury and an injury caused by a neurodegenerative disease, anxiety, epilepsy or stroke.

14. The method according to claim 13, wherein the neurodegenerative disease is selected from the group consisting of Alzheimer's disease, amyotrophic lateral sclerosis (ALS), Parkinson's disease and Huntington's disease.

15. The method according to claim 12, wherein the nervous system injury or pain is located in the peripheral nervous system or the central nervous system.

16. The method according to claim 12, wherein the nervous system injury is a stroke.

17. The method according to claim 16, wherein the stroke is selected from the group consisting of an ischemic stroke, a hemorrhagic stroke, and a hemorrhagic stroke converted from an ischemic stroke.

18. The method according to claim 17, wherein the stroke is an ischemic stroke.

* * * * *